United States Patent
Pless

(10) Patent No.: US 6,466,822 B1
(45) Date of Patent: Oct. 15, 2002

(54) MULTIMODAL NEUROSTIMULATOR AND PROCESS OF USING IT

(75) Inventor: Benjamin D. Pless, Atherton, CA (US)

(73) Assignee: Neuropace, Inc., Sunnyvale, CA (US)

( * ) Notice: Subject to any disclaimer, the term of this patent is extended or adjusted under 35 U.S.C. 154(b) by 0 days.

(21) Appl. No.: 09/543,450

(22) Filed: Apr. 5, 2000

(51) Int. Cl.$^7$ ................................................ A61N 1/02
(52) U.S. Cl. ...................................................... 607/45
(58) Field of Search ...................... 607/44, 45; 600/544

(56) References Cited

U.S. PATENT DOCUMENTS

| | | |
|---|---|---|
| 3,531,561 A | 9/1970 | Trehu |
| 3,565,066 A | 2/1971 | Roaf et al. |
| 3,636,956 A | 1/1972 | Schneider |
| 3,960,151 A | 6/1976 | Kuhn |
| 3,993,046 A | 11/1976 | Fernandez et al. |
| 4,429,690 A | 2/1984 | Angelino-Pievani |
| 4,523,591 A | 6/1985 | Kaplan et al. |
| 4,566,464 A | 1/1986 | Piccone et al. |
| 4,702,254 A | 10/1987 | Zabara |
| 4,781,183 A | 11/1988 | Casey et al. |
| 4,867,164 A | 9/1989 | Zabara |
| 4,905,680 A | 3/1990 | Tunc |
| 4,979,511 A | 12/1990 | Terry, Jr. |
| 5,025,807 A | 6/1991 | Zabara |
| 5,031,618 A | 7/1991 | Mullett |
| 5,129,903 A | 7/1992 | Luhr et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |

(List continued on next page.)

FOREIGN PATENT DOCUMENTS

| | | |
|---|---|---|
| DE | 8528003 | 2/1986 |
| DE | 8706912 | 10/1987 |
| DE | 3701765 C1 | 6/1988 |
| DE | 4028021 C1 | 5/1991 |

(List continued on next page.)

OTHER PUBLICATIONS

Andriano, K.P. et al. (1994). "Processing and Characterization of Absorbable Polyactide Polymers for Use in Surgical Implants," *Journal of Applied Biomaterials* 5:133–140.

Chkhenkeli, S.A. and Chkhenkeli, I.S. (1997). "Effects of Therapeutic Stimulation of Nucleus Caudatus on Epileptic Electrical Activity of Brain in Patients with Intractable Epilepsy," *Stereotact Funct Neurosurg* 69:221–224.

(List continued on next page.)

*Primary Examiner*—Scott M. Getzow
(74) *Attorney, Agent, or Firm*—Morrison & Foerster LLP

(57) ABSTRACT

This is directed to an implantable multimodal neurostimulator having improved efficacy in treating epilepsy and other neurological disorders and to processes of using that neurostimulator. The neurostimulator itself generally has two modes of electrical stimulation: the first involves delivering a non-responsive electrical stimulation signal which is applied to the central nervous system to reduce the likelihood of a seizure or other undesirable neurological even from occurring, and a second mode that involves delivering electrical stimulation signal or signals when epileptiform waveforms are impending or extant. The responsive electrical stimulation signal or signals are intended to terminate epileptiform activity, e.g., to desynchronize abnormally synchronous brain electrical activity. Alternatively, the second mode may be used to deliver sensory stimulation, e.g., a scalp or sound stimulation, to the patient rather than deliver electrical stimulation to the patient. Finally, the implanted neurostimulator may be used by a physician to induce epileptiform activity and then verify the effectiveness of the parameters of the first and second neurostimulation signal or signals.

59 Claims, 6 Drawing Sheets

U.S. PATENT DOCUMENTS

| | | |
|---|---|---|
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,293,879 A | 3/1994 | Vonk et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,330,515 A | 7/1994 | Rutecki et al. |
| 5,335,657 A | 8/1994 | Terry, Jr. et al. |
| 5,349,962 A | 9/1994 | Lockard et al. |
| 5,351,394 A | 10/1994 | Weinberg |
| 5,372,598 A | 12/1994 | Luhr et al. |
| 5,413,577 A | 5/1995 | Pollock |
| 5,474,547 A | 12/1995 | Aebischer et al. |
| 5,522,863 A | 6/1996 | Spano et al. |
| 5,531,778 A | 7/1996 | Maschino et al. |
| 5,540,730 A | 7/1996 | Terry, Jr. et al. |
| 5,540,734 A | 7/1996 | Zabara |
| 5,569,250 A | 10/1996 | Sarver et al. |
| 5,571,150 A | 11/1996 | Wernicke et al. |
| 5,604,204 A | 2/1997 | Ammann et al. |
| 5,676,655 A | 10/1997 | Howard, III et al. |
| 5,683,422 A | 11/1997 | Rise |
| 5,707,396 A | 1/1998 | Benabid |
| 5,707,400 A | 1/1998 | Terry, Jr. et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,752,979 A | 5/1998 | Benabid |
| 5,792,186 A | 8/1998 | Rise |
| 5,800,474 A | 9/1998 | Benabid et al. |
| 5,832,932 A | 11/1998 | Elsberry et al. |
| 5,833,709 A | 11/1998 | Rise et al. |
| 5,868,746 A | 2/1999 | Sarver et al. |
| 5,928,272 A | 7/1999 | Adkins et al. |
| 5,938,689 A | 8/1999 | Fischell et al. |
| 5,978,702 A | 11/1999 | Ward et al. |
| 6,006,124 A | 12/1999 | Fischell et al. |
| 6,016,449 A | 1/2000 | Fischell et al. |
| 6,018,682 A | 1/2000 | Rise |
| 6,024,702 A | 2/2000 | Iversen |
| 6,095,148 A | 8/2000 | Shastri et al. |

FOREIGN PATENT DOCUMENTS

| | | |
|---|---|---|
| EP | 0 195 455 A1 B1 | 9/1986 |
| EP | 0 276 153 A2 A3 | 7/1988 |
| EP | 0 290 138 A2 A3 B1 | 11/1988 |
| EP | 0 291 632 A1 B1 B2 | 11/1988 |
| EP | 0 347 658 A1 B1 | 12/1989 |
| EP | 0 491 983 A1 B1 | 7/1992 |
| GB | 2140523 A | 11/1984 |
| GB | 0 433 852 | 3/1996 |

OTHER PUBLICATIONS

Cooper, I.S. et al. (1974). "The Effect of Chronic Stimulation of Cerebellar Cortex on Epilepsy in Man," In *The Cerebellum, Epilepsy, and Behavior*. Cooper, I.S. et al., eds., Plenum Press:New York, pp. 119–171.

Cooper, I.S. et al. (1977/1978). "Safety and Efficacy of Chronic Cerebellar Stimulation," *Appl. Neurophysiol.* 40: 124–134.

Cooper, I.S. and Upton, A.R.M. (1978). "Effects of Cerebellar Stimulation on Epilepsy, the EEG and Cerebral Palsy in Man," In *Contemporary Clinical Neurophysiology (EEG Suppl. No. 34)*. Cobb, W.A. et al., eds., Elsevier Scientific Publishing: Amsterdam, pp. 349–354.

Davis, R. and Emmonds, S.E. (1992). "Cerebellar Stimulation for Seizure Control: 17–Year Study," *Stereotact. Funct. Neurosurg.* 58:200–208.

Eppley, B.L. and Sadove, A.M. (1992). "Effects of Resorbable Fixation on Craniofacial Skeletal Growth: A Pilot Experimental Study," *Journal of Craniofacial Surgery* 3(4):190–196.

Gerlach, K.L. (1993). "In–vivo and Clinical Evaluations of Poly(L–lactide) Plates and Screws for Use in Maxillofacial Traumatology," *Clinical Materials* 13:21–28.

Gotman, J. (1999). "Automatic Detection of Seizures and Spikes," *Journal of Clinical Neurophysiology* 16(2):130–140.

Osario, I. et al (1995). "A Method for Accurate Automated Real–Time Seizure Detection," *Epilepsia*, 36(supplement 4):4, Abstract No. 1.04.

Qu, H. and Gotman, J. (1995). "A Seizure Warning System for Long–Term Epilepsy Monitoring," *Neurology* 45:2250–2254.

Sayler, K.E. et al. (1994). "A Comparative Study of the Effects of Biodegradable and Titanium Plating Systems on Cranial Growth and Structure: Experimental Study in Beagles," *Plastic and Reconstructive Surgery* 93(4):705–713.

Schiff, S. et al. (1994). "Controlling Chaos in the Brain," *Nature* 370:615–620.

Thaller, S.R. et al. (1992). "Use of Biodegradable Plates and Screws in a Rabbit Model," *Journal of Craniofacial Surgery* 2(4):168–173.

Velasco, F. et al. (1995). "Electrical Stimulation of the Centromedian Thalamic Nucleus in Control of Seizures: Long Term Studies," *Epilepsia* 36(1):63–71.

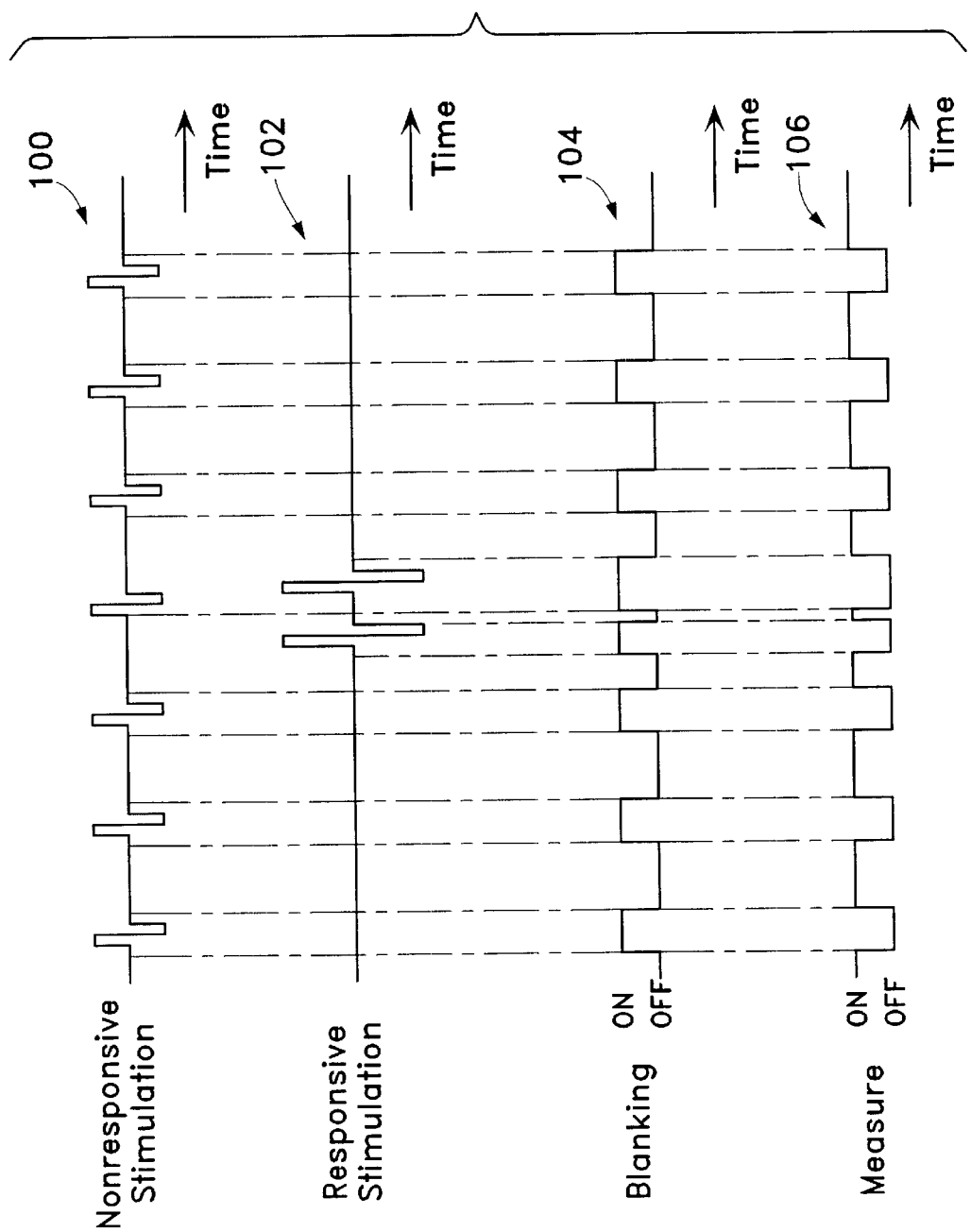

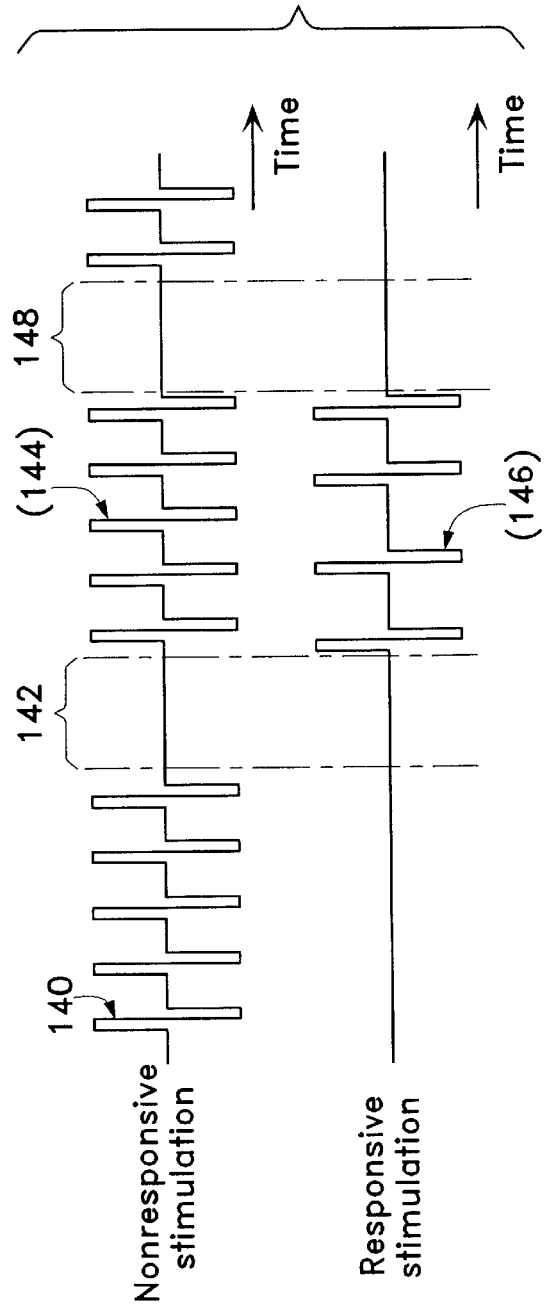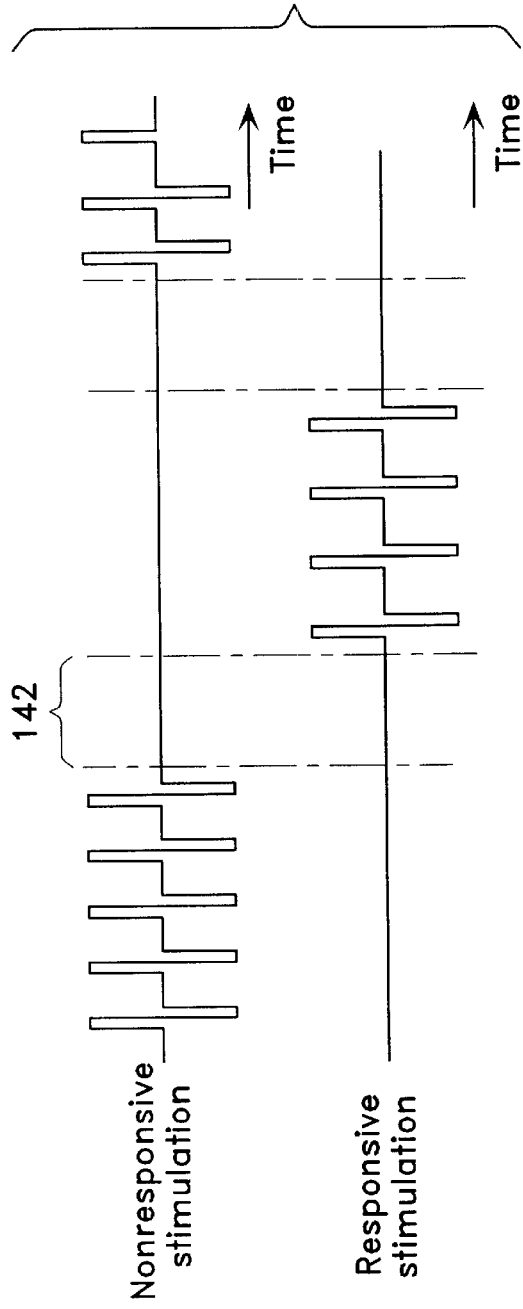

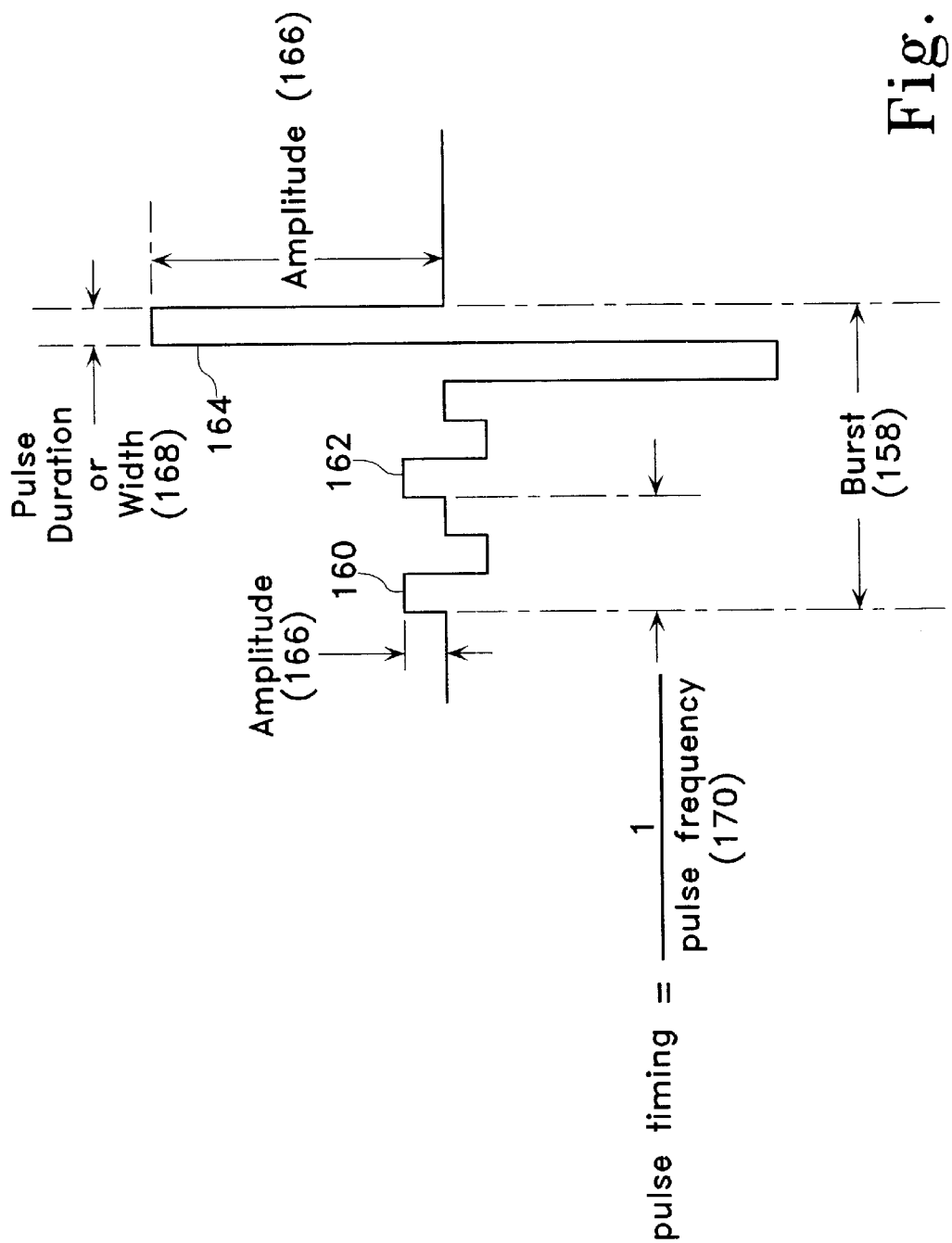

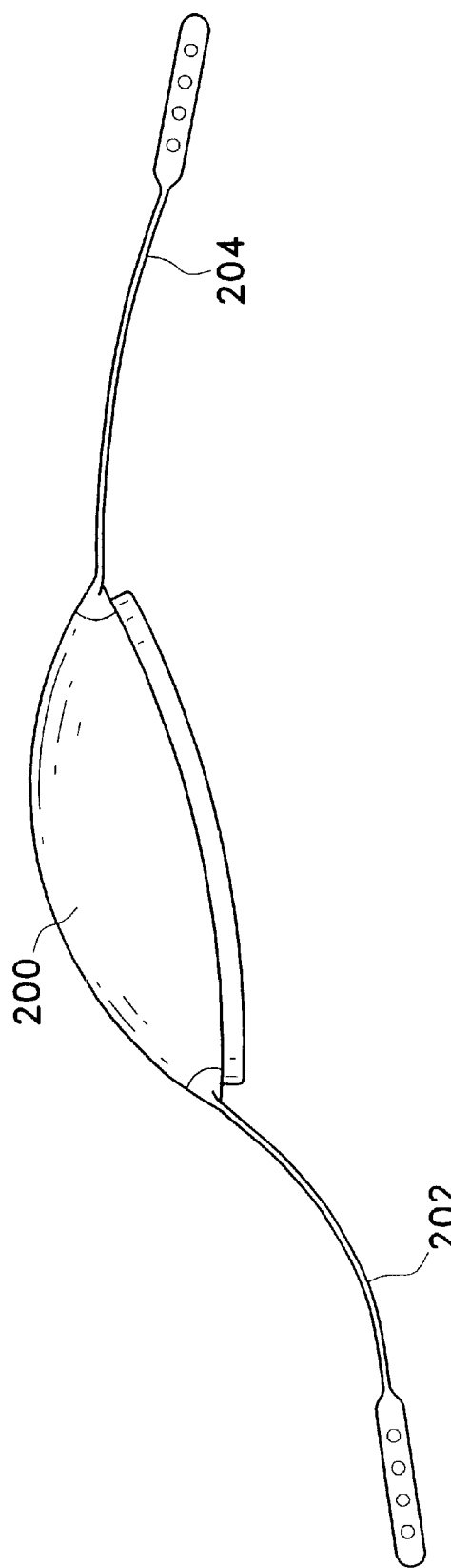

MULTIMODAL NEUROSTIMULATOR AND PROCESS OF USING IT

FIELD OF THE INVENTION

This invention is directed to an implantable neurostimulator having improved efficacy in treating epilepsy and other neurological disorders and to processes of using that neurostimulator. The neurostimulator itself generally involves two modes of electrical stimulation: the first involves delivering a non-responsive electrical stimulation signal which is applied to the central nervous system to reduce the likelihood of a seizure or other undesirable neurological even from occurring, and a second mode that involves delivering electrical stimulation signal or signals when epileptiform waveforms are impending or extant.

The responsive electrical stimulation signal or signals are intended to terminate epileptiform activity, e.g., to desynchronize abnormally synchronous brain electrical activity.

Alternatively, the second mode may be used to deliver sensory stimulation, e.g., a scalp or sound stimulation, to the patient rather than deliver electrical stimulation to the patient.

Finally, the neurostimulator may be used by a physician to induce epileptiform activity and then verify the effectiveness of the parameters of the first and second neurostimulation signal or signals.

BACKGROUND OF THE INVENTION

Epileptic seizures are characterized by excessive or abnormally synchronous neuronal activity. Neurologists recognize a wide variety of seizures. Partial onset seizures begin in one part of the brain; general onset seizures arise throughout the entire brain simultaneously. When partial onset seizures progress to involve much of the brain, they are said to have "secondarily generalized." Some seizures result in the loss of conscious awareness and are termed "complex" seizures. So-called "simple" seizures may involve other symptoms, but consciousness is unimpaired. Seizure symptoms may include sensory distortions, involuntary movements, or loss of muscle tone. The behavioral features of a seizures often reflect a function of the cortex where the abnormal electrical activity is found.

Physicians have been able to treat epilepsy by resecting certain brain areas by surgery and by medication. Brain surgery is irreversible, and is ineffective or is associated with neural morbidity in a sizable percentage of cases. Medication is the most prevalent treatment for epilepsy. It is effective in over half of patients, but in the reminder of the patients, the medication is either ineffective in controlling seizures, or the patients suffer from debilitating side effects. A more promising method of treating patients having epileptic seizures is by electrical stimulation of the brain.

Since the early 1970's, electrical brain stimulators have been used which provide more or less constant stimulation, the stimulation largely being unrelated to detected electrical activity.

Electrical stimulation of the nervous system has been used to suppress seizures. A device is described in Cooper et al. for stimulation of the cerebellum. See, "The Effect of Chronic Stimulation of Cerebellar Cortex on Epilepsy and Man," I. S. Cooper et al in *The Cerebellum, Epilepsy and Behavior,* Cooper, Riklan and Snyder Edition, Pleman Press, New York 1974. Others have utilized devices which stimulated the centro median nucleus of the thalamus. See, "Electrical Stimulation of the Centro Median Thalamic Nucleous in Control of Seizures: Long Term Studies." F. Valasco et al, *Epilepsia,* 36 (1): 63–71, 1995. Chaos Theory has been used to apply stimulation to a seizure focus in vitro to abort the seizure. See, S. Schiff et al, "Controlling Chaos in the Brain," *Nature,* Volume 370, Aug. 25, 1994.

Non responsive electrical stimulation devices have been used for significant periods. The devices and procedures did not constitute a panacea, however. For instance, a 17 year follow-up study shown in Davis et al. ("Cerebellar Stimulation for Seizure Control 17 Year Study," Proceedings of the Meeting of the American Society for Stereotactic and Functional Neurosurgery, Pittsburgh, Pa., Jun. 16–19, 1991 and in Stereotact. Funct. Neurosurg. 1992; 58; 200–208) showed that less than one-half of the patients became seizure free, even though 85% showed some benefit.

In contrast, responsive stimulation, specifically electrical stimulation, that is applied to the brain, has not yet been used to treat patients in long-term studies. This is true even though there are algorithms suitable for detection of the onset of an epileptic seizure. For instance, Qu et al provide an algorithm said to recognize patterns of electrical activity similar to those developed while recording an actual epileptic seizure. See, Qu et al., "A Seizure Warning System for Long-Term Epilepsy Monitoring, *Neurology,*" 1995; 45:2250–2254. Similarly, Osario, et al. have suggested an algorithm applied to signals from intracranial electrodes with good results. See Osario, et al. "A Method For Accurate Automated Real-Time Seizure Detection," *Epilepsia,* Vol. 35, supplement 4, 1995.

None of the cited documents describes procedures in which a non-responsive electrical stimulation signal is applied to the brain in a first mode and, upon detection of impending or of extant epileptiform electrical activity, a second responsive mode of stimulation is applied to the brain either with or without cessation of non-responsive stimulation.

SUMMARY OF THE INVENTION

The invention is an implantable neurostimulator having improved efficacy in treating epilepsy and other neurological disorders and processes of using that neurostimulator. The method generally includes three or more steps. Initially, a non-responsive electrical stimulation signal is applied to the brain in a non-responsive mode. Secondly, some brain electrical activity is detected either during the non-responsive stimulation signal or after the non-responsive stimulation signal is paused. Third, when that detected electrical activity shows an impending or existing epileptiform brain electrical activity, a second electrical stimulation signal is applied to the brain. Alternatively, a sensory stimulation, e.g., sound or scalp twitch, may be directed to the patient in place of or in addition to the second electrical stimulation signal.

The first or non-responsive electrical stimulation signal, may or may not be paused during the second phase as desired. The non-responsive stimulation may be diurnally varied or varied on some other schedule as desired. The brain electrical activity may be detected in a variety of ways including scalp electrodes, cortical electrodes, or the electrical activity may be monitored at a depth within the brain. The responsive electrical stimulation signal may be applied to one or more electrodes placed on or about the brain. If multiple electrodes are chosen, either for measurement of the brain electrical activity or application of the responsive stimulation, the electrodes may be chosen so that they are independently selectable if so desired. The responsive stimulation (and the non-responsive stimulation) may be defined by parameters such as the electrode or electrodes selected, pulse width, interpulse interval, pulse amplitude, pulse morphology, the number of pulses in the burst, the number of bursts, and the intervals between bursts. Each of these parameters for either the responsive or the non-responsive stimulation may be changed or left static during a mode of the process.

The procedure may include a pause of the responsive stimulation for detection of or measurement of brain electrical activity. This may then be followed by either re-commencement of the non-responsive stimulation, or, if the desired cessation of epileptiform activity has not been achieved, by a continuation of the responsive stimulation.

The procedure may also include the step of using the implanted neurostimulator to apply electrical stimulation to the brain under physician control to cause epileptiform activity and a second step of using the implanted neurostimulator to apply a responsive stimulation signal which terminates that epileptiform activity. This permits the neurostimulator to be used to test the effectiveness of the parameters selected for responsive stimulation. The testing may be done before, during, or anytime after implantation of the inventive neurostimulator to assess functionality. in addition, the testing may be used to verify the effectiveness of the non-responsive stimulation parameters by assessing the relative ease or difficulty in initiating epileptiform activity.

In general, the implantable neuro-stimulator includes at least a first brain electrical activity sensor near or in contact with the brain, at least a first stimulator electrode for providing a non-responsive stimulation to the brain and optionally for providing the responsive stimulation, a non-responsive signal source for the first stimulation electrode, one or more (optional) second stimulator electrodes for providing the responsive stimulation, and a responsive stimulation source. The non-responsive and responsive sources may be integrated into a single source if so desired.

Desirably there may be two brain electrodes: the first used for non-responsive stimulation and positioned in or on the cerebellum or in a deep brain structure such as the thalamus, hippocampus or amygdala, the second used for responsive stimulation and placed on or near the seizure focus or a neural pathway involved in sustaining or propagating the epileptiform activity. In some instances there may be only one electrode that is used for both purposes. Conversely, in some variation of the invention, the patient will benefit from a larger number of electrodes being used.

This invention has the following advantages:

1. improved ability to terminate epileptiform activity,
2. less likely to generalize ongoing epileptiform activity,
3. optimally controls seizures by lowering the incidence of seizures as well as treating instances of breakthrough epileptiform activity, and
4. provides for optimization of stimulation parameters programmed into the implanted neurostimulator.

A BRIEF DESCRIPTION OF THE DRAWINGS

FIG. 1A shows a time graph of typical first and second modes and the operation of a blanking operation as used in the inventive process.

FIGS. 2A and 2B show a time graph of alternative methods for detecting electrical activity in the brain by pausing the responsive and non-responsive stimulation of the inventive process.

FIG. 3 shows a graph of conventions used in describing pulse and burst parameters.

FIG. 5 is a depiction of one variation of the inventive neurostimulator having multiple electrodes.

DESCRIPTION OF THE INVENTION

Figure 1B:
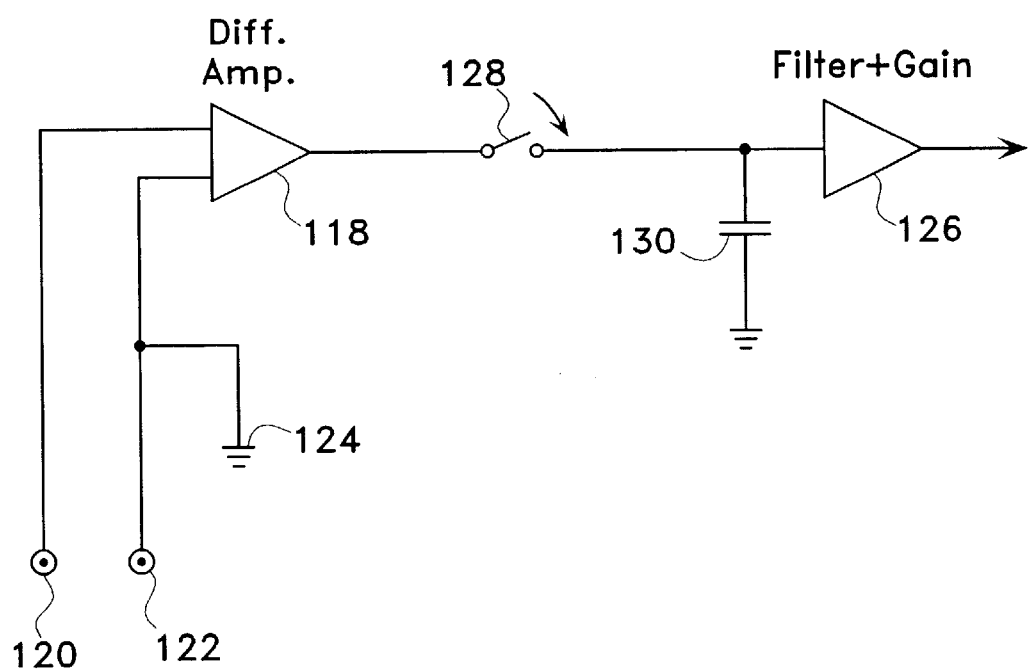
FIG. 1B shows a circuit useful in blanking input to a measurement step as shown in FIG. 1A.

As noted elsewhere, this invention includes a neurostimulation method and devices for practicing that method.

Neurostimulation Methods

In one variation of the invention, the neurostimulation process includes at least two modes. The first mode involves application of a generally "non-responsive" electrical stimulation (or stimulation signal) to the brain. The second mode involves the application of a "responsive" electrical stimulation to the brain or a sensory stimulation elsewhere to the body. Optionally, the process includes steps for detection of electrical activity of the brain, analysis of that activity for impending or existent epileptiform activity, and decision-making steps relating whether to initiate responsive stimulation or to change the parameters of that stimulation.

As used herein, "non-responsive" stimulation refers to the application of electrical therapy intended to lower the probability of a seizure occuring. The parameters (electrode or electrodes used, number of pulses, amplitude, pulse to pulse interval, duration of pulses, etc.) of the non-responsive stimulation, or the application of the non-responsive stimulation may be set or varied as a result of the detection of signals from the patient's body including the nervous system and brain. The parameters of non-responsive stimulation may also be set by a physician. In general, however, and unless the context of the term indicates otherwise, a non-responsive stimulation is one in which the parameters of that stimulation are not controlled or modified in the implantable neurostimulator as a result of the detection of an existing or impending epileptiform event unless done so in conjunction with the use of the response stimulation.

As used herein, "responsive" stimulation refers to the application of electrical therapy in response to the detection of an electrographic (or some other) event indicating an impending or existent seizure. The electrographic event may be the beginning of an electrographic seizure, epileptiform activity, or other features of the EEG that typically occur prior to a seizure. Other events may include motion detection, or external triggering.

As used herein, "seizure" may represent a behavioral seizure wherein clinical evidence of functional or cognitive manifestations of the seizure may be elucidated by testing the patient; or electrographic seizure which refers to abnormalities detectable on the EEG (whether from brain, scalp or other electrodes).

By "stimulation", we mean an electrical signal applied to brain tissue or some type of sensory input applied to the patient to elicit a response. The latter may include such physical motions such as vibration, other electrical signals not to brain tissue (for example a scalp twitch), light flashes, sound pulses, etc.

The term "epileptiform activity" refers to the manifestation on an EEG (cortical, depth, or scalp) of abnormal brain activity whether associated with clinical manifestations or not.

"Electrical stimulation" means the application of an electric field or electric current to biological tissue, "stimulation" means electrical or sensory stimulation.

The brain's electrical activity is detected and analyzed to detect epileptiform activity or to detect such impending activity. If the epileptiform activity is present or impending, the second mode of responsive stimulation is initiated. The results of the analysis of the epileptiform activity may also be used to modify the parameters of the non-responsive stimulation to optimize the suppression of seizures of other undesirable neurological events.

The parameters (electrode or electrodes used, number of pulses, amplitude, frequency, duration of pulses, etc.) of the responsive stimulation may be varied. The variation of the parameters may be based either upon a preprogrammed sequence or based upon some characteristic of the detected epileptiform activity. Additionally, the parameters of the responsive stimulation may be advantageously varied between different episodes of spontaneous epileptiform activity to minimize the tendency of the stimulation itself to predispose the brain to epileptogenesis (also known as "kindling"). Application of the responsive stimulation may be temporally paused or the amplifier blanked during responsive stimulation to allow analysis of the electrical activity of the brain to determine whether the stimulation has had its desired effect. Readjustment of the parameters of the responsive stimulation in the second mode may be repeated as long as it is advantageous in terminating the undesirable epileptiform activity.

This inventive procedure provides for multimodal therapies to be delivered not only to terminate impending or existent epileptiform activity, but also to diminish the likelihood that native seizures will occur. In addition to providing for responsive stimulation delivered upon detecting an indication of epileptiform activity, this invention includes the additional first mode of operation for decreasing the incidence of seizures using non-responsive stimulation. The use of non-responsive stimulation in conjunction with responsive stimulation optimizes the control of seizures by providing a multimodal device that reduces the incidence of seizures, and is also effective at terminating any breakthrough seizures which may occur.

In addition, a testing mode is provided in the implanted device that can be used in conjunction with the responsive and non-responsive modes of operation mentioned above. Once the implantable neurostimulator has been connected to the patient, the testing mode allows for non-invasive verification of the functionality and appropriate programmed settings of the parameters for the responsive and non-responsive modes of operation.

First Mode Stimulation

In its most basic variation, the procedure and device provides neurostimulation in a first mode that is believed to modulate neurotransmitter levels or provide neural desynchronization in the brain resulting in a reduction of seizure incidence. Appropriate use of the non-responsive mode may also be used to reduce the risk of kindling, a phenomenon whereby stimulation may make the neural tissue more prone to epileptogenesis. In addition, any epileptiform electrical activity that may occur is terminated by responsive stimulation in the second mode. As will be discussed below, the first mode (non-responsive) stimulation and the second mode (responsive) stimulation may be delivered from the same electrode, but preferably are delivered from separate electrodes connected to the same implantable neurostimulator. The location of the electrode for the second mode (responsive) stimulation is preferably near the epileptogenic focus. The electrode for first mode (non-responsive) stimulation is preferably in a deep brain structure such as the thalamus, hippocampus, amygdala or is in contact with the cerebellum.

The first mode (non-responsive) stimulation typically is made up of low intensity, short duration pulses delivered at about a 20 to 150 Hz rate. To reduce the likelihood of kindling, pulse to pulse intervals of as much as a second or more may be used for typically 15 minutes or more. The parameters for application of the non-responsive stimulation may be varied according to circadian rhythms. In particular, for some patients, it will be advantageous to alter the stimulation patterns before or during normal sleep times to avoid disrupting sleep patterns, particularly REM sleep.

Responsive Stimulation

As noted above, the responsive stimulation is initiated when an analysis of the brain's electrical activity shows an impending or existent neurological event, such as epileptiform activity. To detect such activity reliably while the first (non-responsive) mode of stimulation is in progress often presents challenges. In some cases, the level of non-responsive stimulation is set at a low enough level, and the sensing electrodes are physically far enough away, that the stimulation does not interfere with detection of brain activity. The use of closely spaced electrodes for either non-responsive stimulation and detection, or both, is helpful in this regard. Often however, it is necessary to take measures to keep the non-responsive stimulation from interfering with detection of brain activity. One method for doing that is to "blank" the detection amplifier (or other detecting circuit component) during the pulse output of the non-responsive stimulation. If that is not effective in eliminating the interference, it may be necessary to periodically pause application of the non-responsive stimulation to allow detection of brain activity.

FIG. 1A shows the known concept of "blanking" in this inventive procedure. We show in the uppermost portion in the drawing a representative non-responsive stimulation signal (100) as a function of time. The pulse width of each stimulation pulse is exaggerated for clarity. In practice, a typical pulse width of 0.2 msec could be used, and the pulse to pulse interval would be about 20 msec. Similarly, just below the non-responsive stimulation (100) is a representative responsive stimulation (102) which has been initiated as the result of detected electrical neurological activity. During the period just before and during each of the stimuli, the input to some component of the detecting function, typically an amplifier, is "blanked" to prevent detecting the stimuli as if they were signals generated by the brain. The blanking is terminated a short period after the pulse ceases. For instance, although the entire stimulation pulse duration is about 0.2 msec, the entire blanking period per pulse might be about 1.0 msec. For a pulse-to-pulse interval of 20 msec, 95% of the time remains available for detecting brain activity. The blanking signal (104) shows the gating time (not to scale) which is used to prevent the sensors from passing information to the related sensing and detecting equipment during the time the stimulation is imposed. Curve (104) shows the "on-off" states for the blanking. The dashed lines from the non-responsive stimulation (100) and a responsive stimulation (102) depict how the blanking periods are formed.

The typical stimulation pulses shown in FIG. 1A are biphasic and typically have a duration of 0.025 to 0.50 milliseconds per phase. The blanking signal (104) slightly precedes and lasts longer than the stimulation pulses to assure that no stimulation artifact disturbs the measurement. The overall duration of the blanking time desirably is typically 1 to 5 milliseconds.

FIG. 1B shows a conceptual circuit which may be used to cause blanking as shown in FIG. 1A. The differential amplifier (118) which detects brain activity has two electrodes (120) and (122). One electrode (122) may be connected to a ground reference (124), which ground reference (124) may be either in the brain or elsewhere in or on the patient's body. The electrical signal detected from the brain is amplified by a differential amplifier (118) before getting additional filtering and amplification by amplifier (126). Blanking switch (128) interposed between differential amplifier (118) and amplifier (126) is usually closed allowing the signal from the brain to be amplified and filtered. During stimulation, the blanking switch (128) is momentarily opened to keep the electrical artifact from the various stimulation pulses from corrupting the output of amplifier (126). When the blanking switch (128) is opened, capacitor (130) keeps the input of amplifier (126) stable in a "track-and-hold" fashion until blanking switch (128) is closed.

In some cases it may be advantageous to add gain reduction to the first ampifier stage and/or autozeroing to further minimize the effect of transients caused by stimulation.

As noted above, another variation of the step for detecting the electrical activity of the brain amidst intermittent instances of stimulation is depicted in FIGS. 2A and 2B. In this variation, instead of blanking the input to the amplifier, the various electrical stimulation signals are paused or stopped for a discrete period, during which the measurement of neuroelectrical activity may be made.

FIG. 2A shows a situation in which non-responsive stimulation (140) (shown here with an exaggerated pulse width for clarity) has been applied to the patient and continues to a first quiet or quiescent period (142) during which monitoring of brain electrical activity is performed. In this variation, whether or not epileptiform activity is found to be approaching or is existing during this initial monitoring period (142), the non-responsive stimulation (140) is restarted (144).

In any event, returning to the first variation shown in FIG. 2A, in this example, pending or existent epileptiform electrical activity is detected in some part of the brain during the initial monitoring period (142) and the responsive stimulation (146) is initiated. In this variation, the non-responsive stimulation (144) continues. Later, both the non-responsive stimulation (144) and the responsive stimulation (146) are then temporally paused for monitoring during the subsequent monitoring period (148) to determine whether epileptiform activity has ceased. The responsive stimulation (146) and non-responsive stimulation (144) may be paused simultaneously, or one may cease before the other. In the instance depicted in FIG. 2A, the epileptiform activity was terminated and the responsive stimulation (146) is not re-initiated after the subsequent monitoring period (148). Of course, as is discussed below, the responsive stimulation (146) is re-initiated, it may be re-initiated either with or without being modified in some fashion.

There are several methods of predicting an impending seizure. The methods include monitoring or detection of EEG synchronization from multiple brain sites and a shift in the energy spectrum. A preferred monitoring scheme is detection of a shift in phase-space parameters. When such a shift occurs, it indicates that a seizure is likely to occur soon, e.g., within the next two to sixty minutes. Under such circumstances, the inventive neurostimulation process may both modify the non-responsive parameters of stimulation and initiate the stimulation. The stimulation changes the underlying dynamics of the brain which results in a reduced likelihood of the impending seizure occurring. Of course, if a seizure occurs, or if the monitoring scheme determines that a seizure is imminent in less than a minute, the responsive mode of stimulation is applied to terminate it.

FIG. 2B shows essentially the same scheme as that shown in FIG. 2A with the major exception that the variation found in FIG. 2B eliminates the non-responsive stimulation signal (144 in FIG. 2A) after the initial monitoring period (142). This variation can be determined either by the decision-making devices of this invention or by pre-programming.

The second electrical stimulation signals in each of FIGS. 1A, 1B, 2A, and 2B are depicted as trains of biphasic pulses. FIG. 3 depicts the terminology used in discussing those signals.

In FIG. 3 is shown a burst (158) of three pulses (160, 162, and 164). The first two pulses (160, 162) are of low amplitude—the term "amplitude" (166) and the physical meaning may be seen in FIG. 3. Amplitude may refer to peak amplitude or average amplitude for non-square pulses. It may refer to any phase of a pulse if the pulse is multiphasic. Amplitude may also be used to describe either the voltage or current for an electrical pulse. The "pulse duration" (168) or time-length of the pulse is depicted as well. Finally, the "pulse-to-pulse interval" (170) of the pulses is the time between pulses.

As noted above, it is within the scope of this invention to vary the electrode used and the parameters of the pulses or of the burst, as shown in FIG. 3, for both the responsive and non-responsive modes of stimulation.

FIGS. 4A to 4F show a number of variations of the pulse and burst makeup, which pulse and parameters may be varied either during a responsive electrical stimulation or may be varied from burst to burst.

Figure 4A:
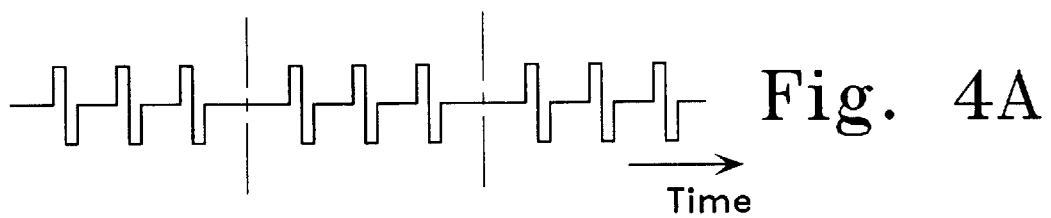
FIGS. 4A–4F show time graphs of exempletive changes in pulse and burst parameters useful in the inventive process.

FIG. 4A shows a simple sequence of bursts having pulses of the same frequency and amplitude in each pulse.

Figure 4B:
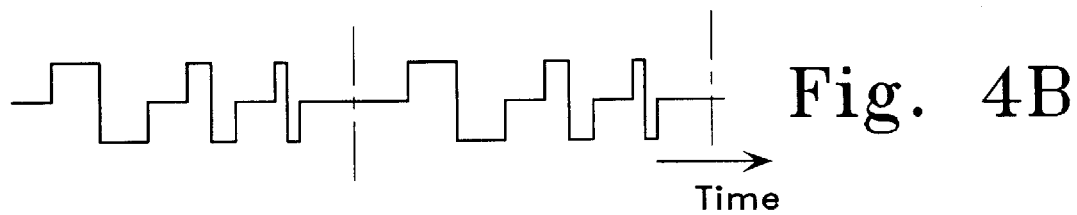

FIG. 4B shows a burst of three pulses in which the duration of the pulses varies as a function of time.

Figure 4C:
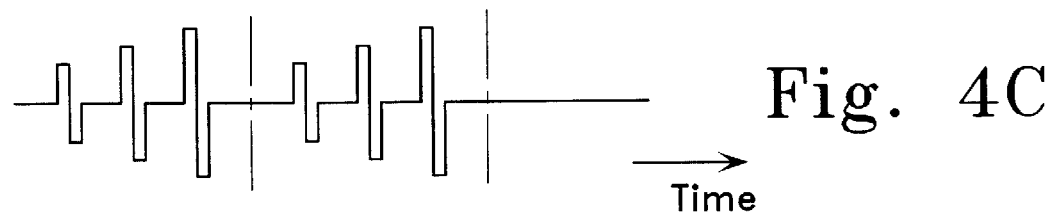

FIG. 4C shows a pair of bursts in which the amplitude of the pulses varies during each burst.

Figure 4D:
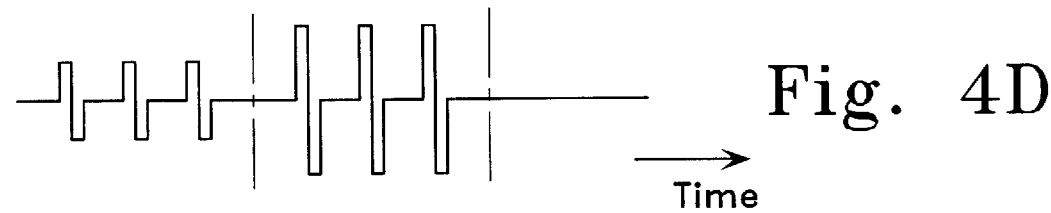

FIG. 4D shows a pair of bursts in which the amplitude of the pulses is increased during the second pulse.

Figure 4E:
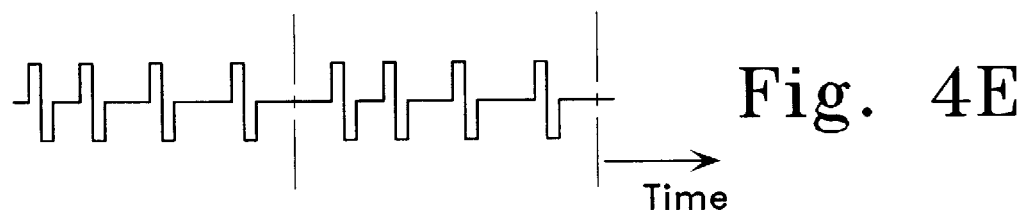

FIG. 4E shows a variation in which the pulse to pulse interval is varied within a burst. This variation is highly desirable in de-synchronizing neuronal activity. The range of pulse to pulse intervals may be varied randomly or changed in a systematic fashion, such as incrementing or decrementing the pulse to pulse interval within a burst.

Figure 4F:
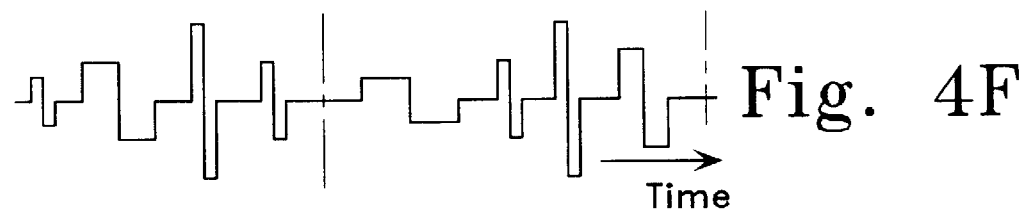

FIG. 4F depicts another variation of the invention which desynchronizes brain activity to terminate epileptiform activity by spatially desynchronizing activity in the vicinity of the stimulation electrode. To accomplish this, various individual pulse parameters, e.g., pulse spacing, duration or width, and amplitude, within a burst may be varied, particularly in a random, pseudo-random, or fractal fashion. Shorter duration pulses (on the order of 50 to 150 microseconds) tend to directly depolarize smaller diameter nerve cells. Longer pulses (100 to 500 microseconds) depolarize larger diameter nerve cells. By varying pulse amplitude, the individual pulses may be tailored directly to depolarize different neural tissue. Lower amplitude pulses directly depolarize tissue in the immediate vicinity of the electrode; higher amplitude pulses directly depolarize tissue both near the electrode and at some distance from the electrode. By varying the amplitude of the pulses within a burst, local tissue can be depolarized at a higher rate than tissue somewhat distant from the electrode.

Since the tissue disposed near an electrode may have highly variable anatomy, it is anticipated that any or all of the parameters described (pulse to pulse interval, pulse amplitude, the use of hyperpolarizing pulses, pulse width, etc.) may be varied alone or in combination to optimize the ability of a burst to terminate epileptiform activity in the brain while improving the safety of the burst by reducing the likelihood of inducing epileptiform activity or generalizing such pre-existing activity.

In addition to producing bursts having pulse intervals having pre-set or absolute time increments, this inventive procedure includes the improvement of setting the pulse to pulse interval based upon the detected temporal interval of the epileptiform activity as sensed by the electrodes detecting the brain electrical activity. In this mode of operation, the rate of the sensed epileptiform activity is detected and measured. The rate of the detected activity is used to modulate the rate, or the average rate, of the burst used to terminate the epileptiform activity perhaps as depicted in FIG. 4F.

It is highly desirable to synchronize initiation of a responsive stimulation burst with certain parameters of the sensed EEG. As is described with greater particularity in Ser. No. 09/543,264 the entirety of which is incorporated by reference) the initiation of the responsive stimulation burst may be delayed for a calculated period that varies from 0 to 100% of the detected EEG interval.

For the purposes of this invention, a burst (in this variation and in each of the others described herein) may be any number of pulses, but typically is in the range from 1 to 100 pulses. After the burst is delivered, the EEG is re-examined, and if the epileptiform activity was not terminated, a subsequent burst is delivered. As was the case above, the subsequent burst may have the same signal parameters as the first burst, may re-adapt to the changing EEG rate, or may have new parameters to more aggressively attempt to terminate the epileptiform activity, e.g., higher pulse or burst rate, more pulses, higher amplitude, or modified pulse to pulse intervals, such are shown in FIGS. 4A to 4F.

Determination of Threshold Values

The following inventive procedures may be used to verify the effectiveness of the implanted neurostimulator and to determine various stimulation parameters for responsive and non-responsive stimulation.

For instance, to verify pulse parameters for effective termination of epileptiform activity after the neurostimulator has been implanted, the following procedure may be used. An epileptiform-inducing stimulation is introduced into the brain under physician control using the implanted neurostimulator thereby initiating epileptiform activity. A responsive stimulation described by the stimulation signal parameters outlined above, e.g., selected electrode, pulse width, pulse-to-pulse interval, pulse amplitude, number of pulses in a burst, etc., is applied to the brain. The stimulation signal parameters are varied until the epileptiform activity ceases.

The steps of initiating epileptiform activity using the implanted neurostimulator, varying stimulation parameters, checking for stimulation effectiveness, and incrementing stimulation parameters may be repeated until a satisfactory cessation of the epileptiform activity is achieved.

Similarly, the efficacy or threshold values associated with operation of the non-responsive mode may be determined. The efficacy of the non-responsive mode is determined by the physician providing increasingly more severe epileptiform-causing stimulation using the implanted neurostimulator until epileptiform activity begins. The more difficult it is to induce the epileptiform activity, the better the non-responsive mode is functioning. By increasing the length of the burst, and/or the amplitude of the pulses within a burst, it is possible for the physician to determine the ease or difficulty with which epileptiform activity may be induced. By comparing how resistant the brain is to the induction of epileptiform activity when the non-responsive stimulation is either activated or not, or with differing burst parameters for the non-responsive stimulation the physician can optimally set the parameters of the non-responsive stimulation.

Implantable Neurostimulator

This inventive device includes a neurostimulator central unit and at least one electrode. The neurostimulator central unit includes the necessary circuitry, e.g., A/D converters, filters, central processing unit(s), digital processing circuits, blanking circuits, power supplies, batteries, signal generators, etc., and programming configured and adapted to perform the steps listed above. Specifically the neurostimulator central unit (200) desirably is as shown in FIG. 6 and is shaped in such a way that it conforms to the shape of the skull, although it need not be so. The neurostimulator central unit should at least contain a non-responsive electrical stimulation source, a responsive stimulation source, (where both sources may be the same circuit operated in two modes), and devices for detecting epileptiform activity and for initiating and for terminating the various non-responsive and responsive electrical stimulation. The neurostimulator assembly should also include at least a first brain electrical activity sensor (202), at least a non-responsive neurostimulator electrode (202), and a responsive electrical neurostimulator electrode (204). A detailed embodiment of this structure may be found in U.S. Pat. No. 6,016,449. The various necessary connectors, leads, and supporting components are also included. The various sensor and neurostimulator functions may be incorporated into one or more electrodes as shown in FIG. 5, however. The various components perform the functions outlined above.

A highly desirable aspect of the inventive device is the use of multiple brain electrodes to provide therapy. The detecting electrodes are preferable in contact with the brain, but, as discussed above, may be scalp electrodes or within the brain tissue. Multiple therapy electrodes enhance the ability of electrical stimulation to desynchronize brain activity in terminating epileptiform activity. Although the same burst may be delivered from a multiplicity of electrodes in the vicinity of the epileptogenic focus, we prefer introducing bursts having different signal parameters, particularly pulse to pulse timing, to the brain from different electrodes to achieve a greater degree of spatial heterogeneity of neural activity and most effectively desynchronize brain activity.

We contemplate that this method of terminating epileptiform activity provides a substantial added benefit in that the lower current densities at the electrodes may be used to affect a larger amount of brain tissue than if a single electrode were used.

The application of multiple electrodes to different parts or regions of the brain also provides a way to treat epilepsy having more than one focus. Electrodes may be placed on or near the various epileptogenic foci. The inventive neurostimulator senses and stimulates independently from each electrode. Optional amplifier blanking eliminates cross talk, and logical flow in the device's software keeps the device from erroneously detecting its own output as epileptiform activity.

This inventive device may utilize independently actuatable, spatially separated electrodes so that those epilepsies having many epileptogenic foci or for which the focus is so diffuse the seizure arises from a large portion of the brain, may be treated. In such a case, it is desirable to place one electrode deep in the brain, preferably in the area of the hippocampus. Additional electrodes may be placed on the surface of the cortex. When epileptiform activity is detected, the device stimulates from the hippocampal region to take advantage of the large number of neural pathways emanating from that area into the cortex. Electrodes on the cortex provide additional electrical access to the brain allowing electrical stimulation to terminate epileptiform activity having a greater spatial extent.

Although preferred embodiments of the invention have been described herein, it will be recognized that a variety of changes and modifications can be made without departing from the spirit of the invention as found in the appended claims.

I claim:

1. A method for treating a disorder in a human brain, comprising the steps of:
   a.) providing at least one non-responsive electrical stimulation to said brain,
   b.) detecting at least one brain electrical activity of said brain, and
   c.) providing at least one responsive stimulation, which is not the non-responsive stimulation, which responsive stimulation is responsive to said at least one brain electrical activity.

2. The method of claim 1 wherein said responsive stimulation is electrical stimulation applied to said human brain.

3. The method of claim 2 wherein blanking is performed when said non-responsive electrical stimulation is provided to said brain.

4. The method of claim 2 wherein said non-responsive electrical stimulation is paused during said detecting.

5. The method of claim 2 further comprising the step of modifying said at least one non-responsive electrical stimulation depending on the time of day.

6. The method of claim 2 wherein said at least one non-responsive electrical stimulation is applied to a first electrode.

7. The method of claim 2 further comprising the step of pausing said at least one non-responsive electrical stimulation during the step of providing said at least one responsive stimulation to said brain.

8. The method of claim 2 wherein said at least one non-responsive electrical stimulation continues during the step of providing said at least one responsive stimulation to said brain.

9. The method of claim 2 wherein said responsive electrical stimulation has responsive electrical stimulation signal parameters and further comprising the step of changing at least one of said responsive electrical stimulation signal parameters during the step of providing said at least one responsive electrical stimulation to said brain.

10. The method of claim 9 wherein said at least one responsive electrical stimulation signal parameter is selected from the group consisting of selected electrode, pulse width, pulse-to-pulse interval, pulse amplitude, number of bursts, and number of pulses in burst.

11. The method of claim 10 wherein at least one responsive electrical stimulation is at least one burst.

12. The method of claim 10 wherein said at least one responsive electrical stimulation signal parameter varies during said burst.

13. The method of claim 10 wherein said at least one responsive electrical stimulation signal parameter is pulse amplitude and the pulse amplitude varies during said burst.

14. The method of claim 10 wherein at least two of said responsive electrical stimulation signal parameters vary during said burst.

15. The method of claim 10 wherein said at least one responsive electrical stimulation signal parameter is pulse-to-pulse interval and said pulse-to-pulse interval varies during said burst.

16. The method of claim 15 wherein said pulse-to-pulse interval is varied based on measured intervals of said brain electrical activity.

17. The method of claim 2 wherein said at least one responsive electrical stimulation is applied to said first electrode.

18. The method of claim 2 wherein said at least one responsive electrical stimulation is applied to a second electrode.

19. The method of claim 18 wherein multiple responsive electrical stimulations are independently applied to multiple second electrodes.

20. The method of claim 19 wherein said multiple responsive electrical stimulations are responsive to multiple electrical brain activities detected at different parts of the brain.

21. The method of claim 20 wherein said multiple electrical brain activities are independently and selectably measured at different parts of the brain.

22. The method of claim 21 wherein said different parts of the brain include the hippocampus and cortical regions.

23. The method of claim 18 wherein each said second electrical stimulations have different signal parameters.

24. The method of claim 2 further comprising the further steps of terminating the application of at least one of the non-responsive electrical stimulation and the responsive electrical stimulation and re-measuring said at least one brain electrical activity.

25. The method of claim 24 further comprising the step of again providing said at least one responsive stimulation to said brain.

26. The method of claim 24 further comprising the step of providing said non-responsive electrical stimulation to said brain.

27. The method of claim 24 wherein said non-responsive electrical stimulation and the responsive electrical stimulation have signal parameters and further comprising the step of changing at least one of said signal parameters in response to the step of re-detecting said at least one brain electrical activity.

28. The method of claim 1 wherein said detecting is accomplished during a period when neither said non-responsive stimulation nor said responsive electrical stimulation is provided to said brain.

29. The method of claim 1 wherein said at least one responsive stimulation comprises sensory input to the patient.

30. The method of claim 29 wherein said sensory input is selected from vibration, other electrical signals not to brain tissue, scalp twitch, light flashes, and sound pulses.

31. The method of claim 1 wherein the step of detecting said at least one brain electrical activity of said brain comprises detecting said electrical activity simultaneously at different sites in said brain.

32. The method of claim 31 wherein the step of simultaneously measuring said at least one brain electrical activity of said brain comprises measuring said electrical activity at the hippocampus in said brain.

33. The method of claim 31 wherein the step of simultaneously measuring said at least one brain electrical activity of said brain comprises measuring said electrical activity at the cortex in said brain.

34. The method of claim 1 wherein said first electrical activity is measured cortically.

35. The method of claim 1 wherein said first electrical activity is measured at a depth within the brain.

36. The method of claim 1 wherein said first electrical activity is measured on the scalp.

37. The method of claim 1 further comprising the step of initiating epileptiform electrical activity under physician control.

38. A method for determining the efficacy of stimulation signal parameters for terminating epileptiform events using an implanted neurostimulator, comprising the steps of:
   a.) initiating epileptiform electrical activity in a human brain,
   b.) observing said epileptiform electrical activity, and
   c.) providing a stimulation having stimulation signal parameters for terminating said epileptiform electrical activity.

39. The method of claim 38 further comprising the additional steps of changing at least one of said stimulation signal parameters, re-initiating said epileptiform electrical activity, re-observing said epileptiform electrical activity, and providing a stimulation having said changed stimulation signal parameters for terminating said epileptiform electrical activity.

40. The method of claim 39 wherein said at least one stimulation signal parameter is selected from the group consisting of selected electrode, pulse width, pulse-to-pulse interval, pulse amplitude, number of bursts, and number of pulses in burst.

41. The method of claim 38 wherein said stimulation is a responsive electrical stimulation.

42. The method of claim 38 wherein said determining the efficacy of stimulation signal parameters also verifies the function of an implanted neurostimulator.

43. A method of determining the efficacy of stimulation parameters in an implanted neurostimulator comprising the steps of:
   a.) providing to a human brain undergoing non-responsive stimulation, said non-responsive stimulation having selected stimulation parameters, an epileptiform initiating stimulation, having epileptiform initiating stimulation parameters,
   b.) observing electrical activity in said human brain for epileptiform activity,
   c.) if epileptiform activity is neither existent nor imminent in step b.), varying at least one of said epileptiform initiating stimulation parameters and repeating steps a.), b.) and c.) until epileptiform activity is imminent or existent; and
   d.) varying said selected non-responsive stimulation parameters and repeat steps a.), b.) and c.).

44. The method of claim 43 further including the steps of providing non-responsive stimulation to said human brain.

45. The method of claim 43 wherein said epileptiform initiating stimulation parameters are selected from the group consisting of pulse amplitude, burst duration, pulse duration, and pulse-to-pulse interval.

46. The method of claim 43 further comprising the prior steps of establishing a pre-stimulus threshold by the steps of:
   a1.) providing to said human brain an epileptiform initiating stimulation, having minimum epileptiform initiating stimulation parameters
   b1.) observing electrical activity in said human brain for epileptiform activity,
   c1.) if epileptiform activity is neither existent nor imminent in step b1.), increment at least one of said minimum epileptiform initiating stimulation parameters and repeat steps a1.), b1.), and c1.) until epileptiform activity is imminent or existent,
   d1.) providing to said human brain a non-responsive stimulation, said non-responsive stimulation having selected non-responsive stimulation parameters,
   e1.) observing electrical activity in said human brain for epileptiform activity, and
   f1.) if epileptiform activity is existent or imminent in step e1.), vary said non-responsive stimulation parameters until said epileptiform activity can no longer be initiated by application of said minimum epileptiform initiating stimulation parameters to thereby determine threshold non-responsive stimulation parameters.

47. An implantable neurostimulator assembly for modifying an electrical activity in a human brain, comprising in combination:
   a.) at least a first brain electrical activity sensor for sensing electrical activity in said brain,
   b.) at least a first non-responsive electrode,
   c.) at least a first non-responsive electrical signal source connectable to said at least said first non-responsive electrical neurostimulator electrode,
   d.) at least a second responsive electrode,
   e.) at least a second responsive electrical signal source connectable to said at least second responsive electrode, said responsive second electrical signal source initiating a responsive stimulation to said at least a second responsive electrode which is responsive to said brain electrical activity sensed by said at least a first brain electrical activity sensor.

48. The implantable neurostimulator of claim 47 wherein said first non-responsive electrical signal source is configured to pause said non-responsive electrical signal when said second responsive electrical signal is initiated.

49. The implantable neurostimulator of claim 47 wherein said first non-responsive electrical signal source is configured to continue said first non-responsive electrical signal when said second responsive electrical signal is initiated.

50. The implantable neurostimulator of claim 47 wherein said first brain electrical activity sensor comprises multiple sensors.

51. The implantable neurostimulator of claim 47 wherein said multiple brain electrical activity sensors comprises sensors for measuring said at least one brain electrical activity of said brain simultaneously at different sites in said brain.

52. The implantable neurostimulator of claim 51 wherein said sensors are configured to measure said brain activity at least at the hippocampus in said brain.

53. The implantable neurostimulator of claim 51 wherein said sensors are configured to measure said brain activity at least at the cortex in said brain.

54. The implantable neurostimulator of claim 51 wherein said sensors are configured to measure said brain activity cortically.

55. The implantable neurostimulator of claim 51 wherein said sensors are configured to measure said brain activity at a depth within the brain.

56. The implantable neurostimulator of claim 51 wherein said sensors are configured to measure said brain activity on the scalp.

57. The implantable neurostimulator of claim 47 wherein said first non-responsive electrical signal source and said second responsive signal source comprise a single electrical signal source circuit.

58. A method for treating a disorder in a human brain having non-responsive stimulation, comprising the steps of a.) detecting at least one brain electrical activity of said brain, b.) providing at least one responsive stimulation having selected stimulation parameters, which responsive stimulation is responsive to said at least one brain electrical activity, and varying said at least one stimulation parameter of said responsive stimulation upon detection of said brain electrical activity.

59. A method for treating a disorder in a human brain, comprising the steps of:

a.) providing at least one non-responsive electrical stimulation to said brain, and b.) modifying said at least one non-responsive electrical stimulation as a function of the time of day.

* * * * *